US012297181B2

(12) United States Patent
Thomas et al.

(10) Patent No.: US 12,297,181 B2
(45) Date of Patent: May 13, 2025

(54) METHODS TO CHEMICALLY MODIFY CANNABINOIDS

(71) Applicant: Natural Extraction Systems, LLC, Boulder, CO (US)

(72) Inventors: C. Russell Thomas, Boulder, CO (US); Matthew M. DePalo, Aurora, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 996 days.

(21) Appl. No.: 17/267,279

(22) PCT Filed: Aug. 9, 2019

(86) PCT No.: PCT/US2019/045950
§ 371 (c)(1),
(2) Date: Feb. 9, 2021

(87) PCT Pub. No.: WO2020/033859
PCT Pub. Date: Feb. 13, 2020

(65) Prior Publication Data
US 2021/0309628 A1 Oct. 7, 2021

Related U.S. Application Data

(63) Continuation of application No. 16/271,782, filed on Feb. 9, 2019, now Pat. No. 10,669,248.

(60) Provisional application No. 62/717,235, filed on Aug. 10, 2018, provisional application No. 62/803,408, filed on Feb. 8, 2019.

(51) Int. Cl.
*C07D 311/78* (2006.01)
*B01D 5/00* (2006.01)
*C07C 29/80* (2006.01)
*C07C 67/08* (2006.01)

(52) U.S. Cl.
CPC ............ *C07D 311/78* (2013.01); *C07C 29/80* (2013.01); *C07C 67/08* (2013.01); *B01D 5/006* (2013.01)

(58) Field of Classification Search
None
See application file for complete search history.

(56) References Cited

U.S. PATENT DOCUMENTS

| | | |
|---|---|---|
| 2,467,435 A | 4/1949 | Langhurst |
| 2,805,981 A | 9/1957 | Cavin |
| 3,270,437 A | 9/1966 | Lara |
| 4,227,997 A | 10/1980 | Shaddock |
| 4,279,824 A | 7/1981 | McKinney |
| 4,396,487 A | 8/1983 | Strumskis |
| 4,752,307 A | 6/1988 | Asmus |
| 5,002,784 A | 3/1991 | Paré |
| 5,026,549 A | 6/1991 | Coutiere |
| 5,235,992 A | 8/1993 | Sensabaugh, Jr. |
| 5,408,924 A | 4/1995 | Arendt |
| 5,458,897 A | 10/1995 | Paré |
| 6,019,819 A | 2/2000 | Williams |
| 6,248,910 B1 | 6/2001 | Franke |
| 6,365,416 B1 | 4/2002 | Elsohly |
| 6,403,126 B1 | 6/2002 | Webster |
| 6,860,998 B1 | 3/2005 | Wilde |
| 7,001,502 B1 | 2/2006 | Satchwell |
| 7,001,629 B1 | 2/2006 | Mengal |
| 7,344,736 B2 | 3/2008 | Whittle |
| 7,622,140 B2 | 11/2009 | Whittle |
| 7,833,298 B2 | 11/2010 | Larholm |
| 8,062,410 B2 | 11/2011 | Bullinger |
| 8,329,229 B2 | 12/2012 | Gonzalez |
| 8,343,553 B2 | 1/2013 | Hospodor |
| 8,445,034 B1 | 5/2013 | Coles, Jr. |
| 9,038,413 B2 | 5/2015 | Howard |
| 9,987,567 B1 | 6/2018 | Ko |
| 10,159,908 B2 | 12/2018 | Thomas |
| 10,195,159 B2 | 2/2019 | Whittle |
| 10,238,705 B2 | 3/2019 | Speier |
| 10,413,843 B2 | 9/2019 | Ko et al. |
| 10,456,708 B2 | 10/2019 | Thomas |
| 10,617,974 B2 | 4/2020 | Thomas |
| 10,669,248 B2 | 6/2020 | Thomas |
| 10,806,707 B2 | 10/2020 | Finley et al. |
| 10,822,320 B2 | 11/2020 | Thomas |
| 10,881,982 B2 | 1/2021 | Thomas |
| 11,643,402 B2 | 5/2023 | Thomas et al. |
| 11,702,397 B2 | 7/2023 | Thomas et al. |
| 2002/0139097 A1 | 10/2002 | Brilmaker |
| 2004/0049059 A1 | 3/2004 | Mueller |

(Continued)

FOREIGN PATENT DOCUMENTS

| | | |
|---|---|---|
| CA | 2472561 A1 | 8/2002 |
| CN | 201643760 U | 11/2010 |

(Continued)

OTHER PUBLICATIONS

Benmoussa, H. et al., Enhanced solvent-free microwave extraction of Foeniculum vulgare Mill. essential oil seeds using double walled reactor. Arabian Journal of Chemistry (2016) 12:3863-3870.
Filly, A. et al., Solvent-free microwave extraction of essential oil from aromatic herbs: From laboratory pilot industrial scale. Food Chemistry (2013) 150:193-198.
Petrov, V.M. et al., Microwave Absorbing Materials. Inorganic Materials (2001) 37(2):93-98.
Wang, Z. et al., Improved solvent-free microwave extraction of essential oil from dried Cuminum cyminum L. and Zanthoxylum bungeanum Maxim. Journal of Chromatography A (2006) 1102:11-17.
Kanter et al., "Qualitative determination of delta9-tetrahydrocannabinol and delta9-tetrahydrocannabinolic acid in marihuana by high-pressure liquid chromatograph," Journal of Chromatography, 1979, pp. 504-508, vol. 171.

(Continued)

*Primary Examiner* — Noble E Jarrell
(74) *Attorney, Agent, or Firm* — Douglas G. Metcalf

(57) ABSTRACT

Various aspects of this disclosure relate to methods to lower the activation energy of the cannabinoid decarboxylation reaction by performing the decarboxylation reaction in the gas phase.

26 Claims, 3 Drawing Sheets

(56) References Cited

U.S. PATENT DOCUMENTS

| | | |
|---|---|---|
| 2004/0147767 A1 | 7/2004 | Whittle |
| 2004/0147769 A1 | 7/2004 | Davis |
| 2004/0187340 A1 | 9/2004 | Chemat |
| 2005/0042172 A1 | 2/2005 | Whittle |
| 2005/0172802 A1 | 8/2005 | Betting |
| 2009/0054711 A1 | 2/2009 | Lawrence |
| 2010/0119606 A1 | 5/2010 | Whittle |
| 2011/0133120 A1 | 6/2011 | McGhee |
| 2012/0012002 A1 | 1/2012 | Kaneko |
| 2012/0157719 A1 | 6/2012 | Teles |
| 2013/0240347 A1 | 9/2013 | Hackleman |
| 2014/0001027 A1 | 1/2014 | Balass |
| 2014/0113010 A1 | 4/2014 | Hospodor |
| 2014/0193303 A1 | 7/2014 | Ellis |
| 2014/0271940 A1 | 9/2014 | Wurzer |
| 2015/0068113 A1 | 3/2015 | Conner |
| 2015/0252286 A1 | 9/2015 | Scialdone |
| 2016/0038437 A1 | 2/2016 | Whittle |
| 2016/0053199 A1 | 2/2016 | Clodoveo |
| 2016/0228385 A1 | 8/2016 | Sievers |
| 2018/0000857 A1 | 1/2018 | Kotra et al. |
| 2018/0078874 A1 | 3/2018 | Thomas |
| 2018/0296617 A1 | 10/2018 | Rivas |
| 2019/0151171 A1 | 5/2019 | Johnson |
| 2020/0290988 A1 | 9/2020 | Thomas |
| 2023/0101492 A1 | 3/2023 | Thomas |
| 2023/0312502 A1 | 10/2023 | Thomas |
| 2024/0092752 A1 | 3/2024 | Thomas |

FOREIGN PATENT DOCUMENTS

| | | | |
|---|---|---|---|
| CN | 101553702 B | 6/2012 | |
| CN | 105943615 A | 9/2016 | |
| EP | 2644039 A1 | 10/2013 | |
| EP | 3453397 A1 | 3/2019 | |
| FR | 2742358 A1 | 6/1997 | |
| GB | 635121 | 4/1950 | |
| GB | 2372714 A | 9/2002 | |
| JP | 4388715 B2 | 11/2002 | |
| JP | 4849578 B1 | 1/2012 | |
| WO | 2002089945 A2 | 11/2002 | |
| WO | 2014000077 A1 | 1/2014 | |
| WO | 2015049585 A2 | 4/2015 | |
| WO | WO-2015070167 A1 * | 5/2015 | ............. A61K 36/18 |
| WO | 2016153347 A1 | 9/2016 | |
| WO | 2016161420 A1 | 10/2016 | |
| WO | 2018009514 A1 | 1/2018 | |
| WO | 2018102711 A1 | 6/2018 | |

OTHER PUBLICATIONS

Veress et al., "Determination of cannabinoid acids by high-performance liquid chromatography of their neutral derivatives formed by thermal decarboxylation: I. Study of the decarboxylation process in open reactors," Journal of Chromatography, 1990, pp. 339-347, vol. 520.

* cited by examiner

METHODS TO CHEMICALLY MODIFY CANNABINOIDS

CROSS-REFERENCE TO RELATED APPLICATIONS

This patent application is the U.S. National Stage Under 35 § U.S.C. 371 of International Application No. PCT/US19/45950, filed Aug. 9, 2019, which claims priority to U.S. patent application Ser. No. 16/271,782, filed Feb. 9, 2019, which granted as U.S. Pat. No. 10,669,248; U.S. Patent Application No. 62/803,408, filed Feb. 8, 2019; and U.S. Patent Application No. 62/717,235, filed Aug. 10, 2018, each of which is incorporated by reference in its entirety.

BACKGROUND

Industrial hemp and other forms of *cannabis* contain a variety of different cannabinoids, which predominantly each contain a carboxyl group. These cannabinoid carboxylic acids bind the human cannabinoid receptors with relatively low affinity. The production of industrial hemp extract, therapeutic pharmaceuticals, and psychoactive drugs from *cannabis* therefore generally utilizes a decarboxylation step, which typically involves prolonged heating. This heating generally results in thermal degradation products and other undesirable chemical modifications. Improved methods to decarboxylate cannabinoids remain desirable.

SUMMARY

Various aspects of this patent document relate to a method to chemically-modify a cannabinoid molecule, comprising: providing a composition comprising cannabinoids, in which the cannabinoids comprise a native cannabinoid molecule, the native cannabinoid molecule comprises a carboxyl group, and the native cannabinoid molecule is in a liquid phase or a solid phase; contacting the composition with sufficient energy to convert the native cannabinoid molecule into (i) a carbon dioxide molecule and (ii) a modified cannabinoid molecule in a gas phase; contacting the modified cannabinoid molecule with a heat sink to condense the modified cannabinoid molecule into a condensed cannabinoid molecule in a liquid distillate; and collecting the liquid distillate.

In preferred embodiments, the composition comprises an extracted oil that was extracted from a plant material of the genus *Cannabis*, the extracted oil comprises the cannabinoids.

In some embodiments, contacting a composition with sufficient energy to convert a native cannabinoid molecule into (i) a carbon dioxide molecule and (ii) a modified cannabinoid molecule in a gas phase comprises contacting the composition with 0.0004 kilowatt hours to 0.04 kilowatt hours of energy per gram of the composition. In some specific embodiments, contacting a composition with sufficient energy to convert a native cannabinoid molecule into (i) a carbon dioxide molecule and (ii) a modified cannabinoid molecule in a gas phase comprises contacting the composition with 0.0004 kilowatt hours to 0.004 kilowatt hours of energy per gram of the composition.

In some embodiments, the sufficient energy is less than 100 kilojoules of energy per gram of the composition. In some specific embodiments, the sufficient energy is at least 50 joules and no greater than 100 kilojoules of energy per gram of the composition. In some very specific embodiments, the sufficient energy is at least 2 kilojoules and no greater than 50 kilojoules per gram of the composition.

In some embodiments, the sufficient energy is less than 10 kilojoules of energy per gram of the composition.

In some embodiments, contacting a composition with sufficient energy to convert a native cannabinoid molecule into (i) a carbon dioxide molecule and (ii) a modified cannabinoid molecule in a gas phase comprises contacting the composition with energy at a rate of less than 100 kilowatts of power per gram of the composition for a duration of less than 60 seconds.

In some embodiments, a method comprises contacting a composition with a heated gas having a temperature of 190 to 250 degrees Celsius.

In some embodiments, a method comprises contacting a composition with a heated surface having a temperature of 190 to 250 degrees Celsius.

In some embodiments, a composition has a surface-area-to-volume ratio greater than 1000 per meter.

In some embodiments, both (a) contacting a composition with sufficient energy to convert a native cannabinoid molecule into (i) a carbon dioxide molecule and (ii) a modified cannabinoid molecule in a gas phase and (b) condensing the modified cannabinoid molecule into a condensed cannabinoid molecule are completed in less than 60 seconds.

In some embodiments, a method comprises directing a composition comprising cannabinoids along a heated path having a length of at least 4 meters, in which the composition is contacted with sufficient energy to convert a native cannabinoid molecule into (i) a carbon dioxide molecule and (ii) a modified cannabinoid molecule in a gas phase in the heated path.

In some embodiments, a method comprises directing a composition comprising cannabinoids along a heated path at a rate of at least 2 meters per second.

In some embodiments, a method comprises coating a heated surface with a composition comprising cannabinoids at a surface-area-to-volume ratio of the composition that is greater than 500 per meter prior to converting a native cannabinoid molecule into a carbon dioxide molecule and a modified cannabinoid molecule. In some specific embodiments, the method comprises contacting the composition with sufficient energy from the heated surface.

In some embodiments, the gas phase comprises less than 5 percent by volume molecular oxygen.

In some embodiments, the heated surface is a surface of a thin-film evaporator. An example of a thin-film evaporator is the Short Path Distillation Plant VKL 70-5 (ROOT SCIENCES, Washington, United States).

In some embodiments, a composition comprises cellulose, and a method comprises both separating a modified cannabinoid molecule in a gas phase from the cellulose and collecting the cellulose, in which: the cellulose is suspended in the gas phase; and the separating occurs both (a) after converting a native cannabinoid molecule into (i) a carbon dioxide molecule and (ii) the modified cannabinoid molecule in the gas phase, and (b) prior to contacting the modified cannabinoid molecule with a heat sink. In some embodiments, a composition comprises chlorophyll, and a method comprises both separating a modified cannabinoid molecule in a gas phase from the chlorophyll and collecting the chlorophyll, in which: the chlorophyll is suspended in the gas phase; and the separating occurs both (a) after converting a native cannabinoid molecule into (i) a carbon dioxide molecule and (ii) the modified cannabinoid molecule in the gas phase, and (b) prior to contacting the modified cannabinoid molecule with a heat sink.

In some specific embodiments, a native cannabinoid molecule is cannabidiolic acid ("CBDA"), a modified cannabinoid molecule is cannabidiol ("CBD"), and a condensed cannabinoid molecule is CBD.

In some specific embodiments, a native cannabinoid molecule is tetrahydrocannabinolic acid ("THCA"), a modified cannabinoid molecule is tetrahydrocannabinol ("THC," which is also known as "delta-9-THC"), and a condensed cannabinoid molecule is THC.

In some embodiments, a method comprises converting at least 75% of a native cannabinoid molecule into a condensed cannabinoid molecule per mole of the native cannabinoid molecule. In some embodiments, a method comprises converting at least 85% of a native cannabinoid molecule into a condensed cannabinoid molecule per mole of the native cannabinoid molecule. In some embodiments, a method comprises converting at least 90% of a native cannabinoid molecule into a condensed cannabinoid molecule per mole of the native cannabinoid molecule. In some embodiments, a method comprises converting at least 95% of a native cannabinoid molecule into a condensed cannabinoid molecule per mole of the native cannabinoid molecule.

In some embodiments, a method comprises producing a liquid distillate comprising a condensed cannabinoid molecule and cannabinol ("CBN") at a molar ratio greater than 100:1.

In some embodiments, the method comprises converting less than 2 percent of the native cannabinoid molecule into cannabinol by mole.

In some embodiments, the method is performed such that the liquid distillate comprises cannabinol at a concentration of less than 0.8 percent by weight.

In some embodiments, the method comprises converting less than 0.2 percent of the native cannabinoid molecule into delta-8-tetrahydrocannabinol (delta-8-THC) by mole.

In some embodiments, the composition comprises THCA and THC, and the method converts less than 0.2 percent of the THCA and THC of the composition into delta-8-THC by mole.

In some embodiments, the method is performed such that the liquid distillate comprises the condensed cannabinoid molecule and cannabinol at a molar ratio of greater than 100:1; and the liquid distillate comprises the condensed cannabinoid molecule and delta-8-tetrahydrocannabinol at a molar ratio of greater than 300:1.

In some embodiments, a method comprises producing a product from a liquid distillate in which the product comprises a condensed cannabinoid molecule at a concentration of at least 55% by weight. In some specific embodiments, a method comprises producing a product from a liquid distillate in which the product comprises THC at a concentration of at least 55% by weight.

In some embodiments, a liquid distillate comprises ethanol, and a method comprises evaporating the ethanol to produce a product.

DETAILED DESCRIPTION

The present disclosure describes methods to rapidly decarboxylate cannabinoids while limiting the generation of undesirable side products. Various methods comprise (1) rapidly vaporizing and decarboxylating a cannabinoid, and then (2) contacting the vaporized, decarboxylated cannabinoid with a heat sink to condense the decarboxylated cannabinoid.

Cannabinoids are typically decarboxylated by heating. Traditional hydrocarbon-based extraction methods typically extract cannabinoid carboxylic acids from *cannabis* prior to decarboxylation. The extracted cannabinoid carboxylic acids are typically then converted into activated, decarboxylated cannabinoids by heating in a vacuum oven for several hours. The inventors modelled possible reaction mechanisms and determined that cannabinoid carboxylic acids can self-catalyze the decarboxylation reaction.

Figure 1:
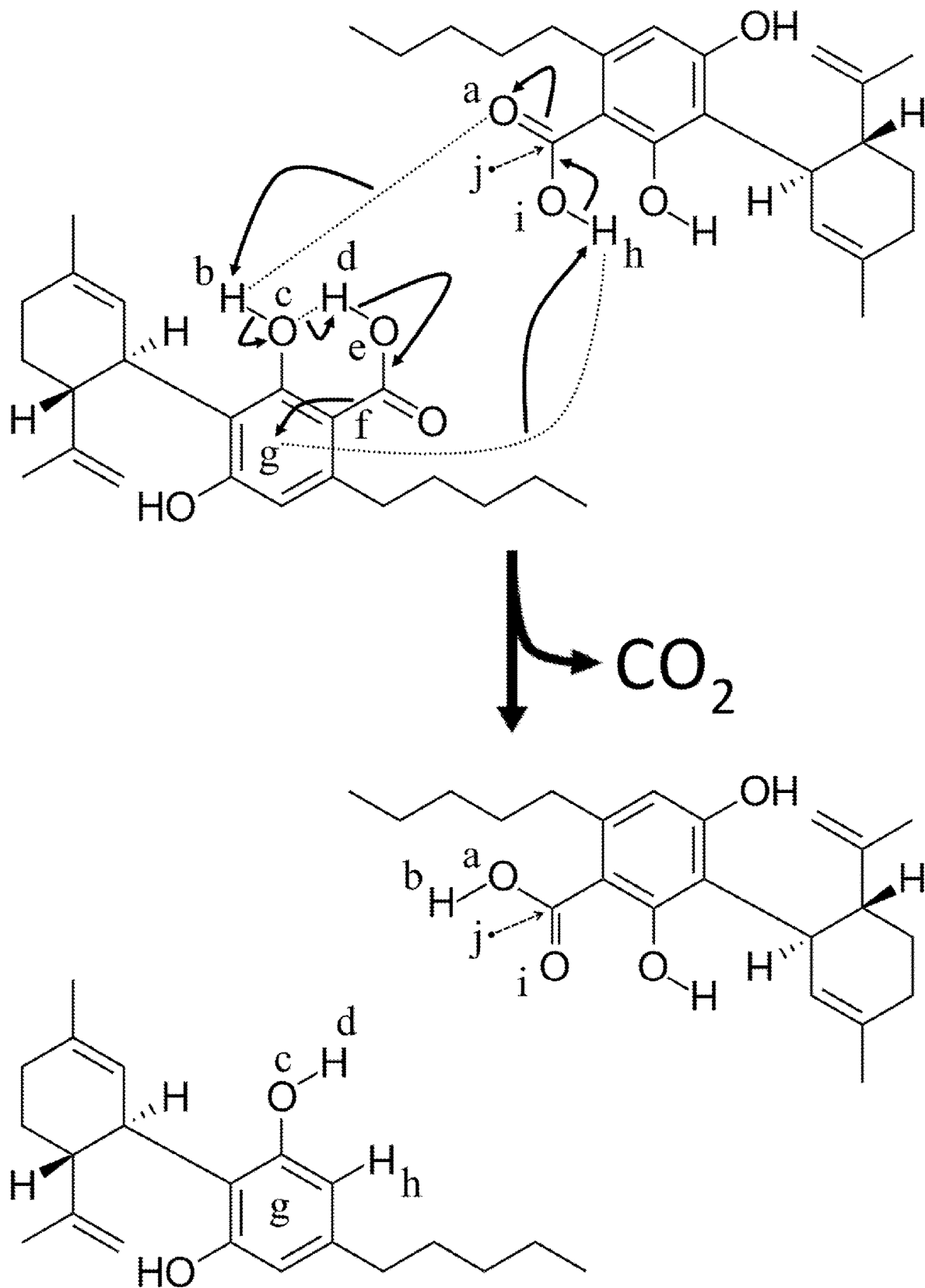
FIG. 1 depicts the skeletal formula of two CBDA molecules before and after a first CBDA molecule catalyzes the decarboxylation of a second CBDA molecule to reform the first CBDA molecule and to produce CBD and carbon dioxide from the second CBDA molecule.

Without being bound by any particular theory, it is believed that decarboxylation can proceed in a single-step, cyclic reaction depicted in FIG. 1, which shows a first 2,4-dihydroxy-3-[(1R,6R)-6-isopropenyl-3-methylcyclohex-2-en-1-yl]-6-pentylbenzoic acid ("cannabidiolic acid"; "CBDA") molecule (FIG. 1, top) catalyzing the decarboxylation of a second CBDA molecule (FIG. 1, bottom). Immediately prior to the reaction, the first and second CBDA molecules form two intermolecular hydrogen bonds denoted by two long dotted lines in FIG. 1. The hydrogen bond depicted by the top-most dotted line is between an electron pair of the carbonyl oxygen of the first CBDA molecule (FIG. 1, "a") and the hydroxyl proton of the second CBDA molecule (FIG. 1, "b"). The hydrogen bond depicted by the bottom-most dotted is between the pi electron cloud of the second CBDA molecule (FIG. 1, "g") and the carboxylic acid proton of the first CBDA molecule (FIG. 1, "h"). An intramolecular hydrogen bond also forms between an electron pair of the hydroxyl oxygen of the second CBDA molecule (FIG. 1, "c") and the carboxylic acid proton of the second CBDA molecule (FIG. 1, "d").

The predicted, single-step, cyclic reaction shown in FIG. 1 proceeds by converting the three hydrogen bonds into covalent bonds, breaking four single bonds, converting two single bonds into double bonds, and converting a double bond into a single bond. The hydrogen bond between an electron pair of the carbonyl oxygen of the first CBDA molecule (FIG. 1, "a") and the hydroxyl proton of the second CBDA molecule (FIG. 1, "b") becomes a covalent bond, which converts the double bond between the carbonyl oxygen (FIG. 1, "a") and the carbonyl carbon (FIG. 1, "j") of the first CBDA molecule into a single bond. The hydroxyl of the second CBDA molecule reforms by converting the hydrogen bond between an electron pair of the hydroxyl oxygen of the second CBDA molecule (FIG. 1, "c") and the carboxylic acid proton of the second CBDA molecule (FIG. 1, "d") into a covalent bond. The extra electron pair of the deprotonated carboxylate oxygen of the second CBDA molecule (FIG. 1, "e") converts the single bond of the deprotonated carboxylate into a double bond, and the electron pair of the carbon-carbon single bond at the 1-position of the second CBDA molecule (FIG. 1, "f") enters the pi electron cloud of the aromatic ring of the second CBDA molecule (FIG. 1, "g") to release the deprotonated carboxylate from the second CBDA molecule as a carbon dioxide molecule. The hydrogen bond between the pi electron cloud of the second CBDA molecule (FIG. 1, "g") and the carboxylic acid proton of the first CBDA molecule (FIG. 1, "h") becomes a covalent bond to replace the deprotonated carboxylate at the 1-position of the second CBDA molecule (which left the second CBDA molecule as a carbon dioxide molecule) with the proton and form a CBD molecule. The extra electron pair of the deprotonated oxygen of the first CBDA molecule (FIG. 1, "i") converts the single bond between the deprotonated oxygen (FIG. 1, "i") and the carbonyl carbon (FIG. 1, "j") into a double bond to reform the carboxylic acid of the first CBDA molecule.

The reaction mechanism described above is represented by arrows in FIG. 1, which depict electron pair pushing. Specific atoms are annotated by the lowercase letters "a"-"e" and "h"-"j" FIG. 1 as described above. The bond that breaks to decarboxylate the second CBDA molecule and release a carbon dioxide molecule is annotated by the lowercase letter "f" in FIG. 1 as described above. The pi electron cloud of the aromatic ring of the second CBDA molecule is annotated by the lowercase letter "g" in FIG. 1 as described above.

The proposed reaction mechanism described above was modeled in three dimensions to determine whether the sterics of the actual CBDA and THCA molecules are compatible with the proposed reaction mechanism. The inventors determined that two CBDA or THCA molecules can form near-perfect hydrogen bond lengths and geometries without steric clashes or significant entropic penalty provided that a first CBDA or THCA molecule can interact with a second CBDA or THCA molecule at an approximate orthogonal orientation.

Figure 2:
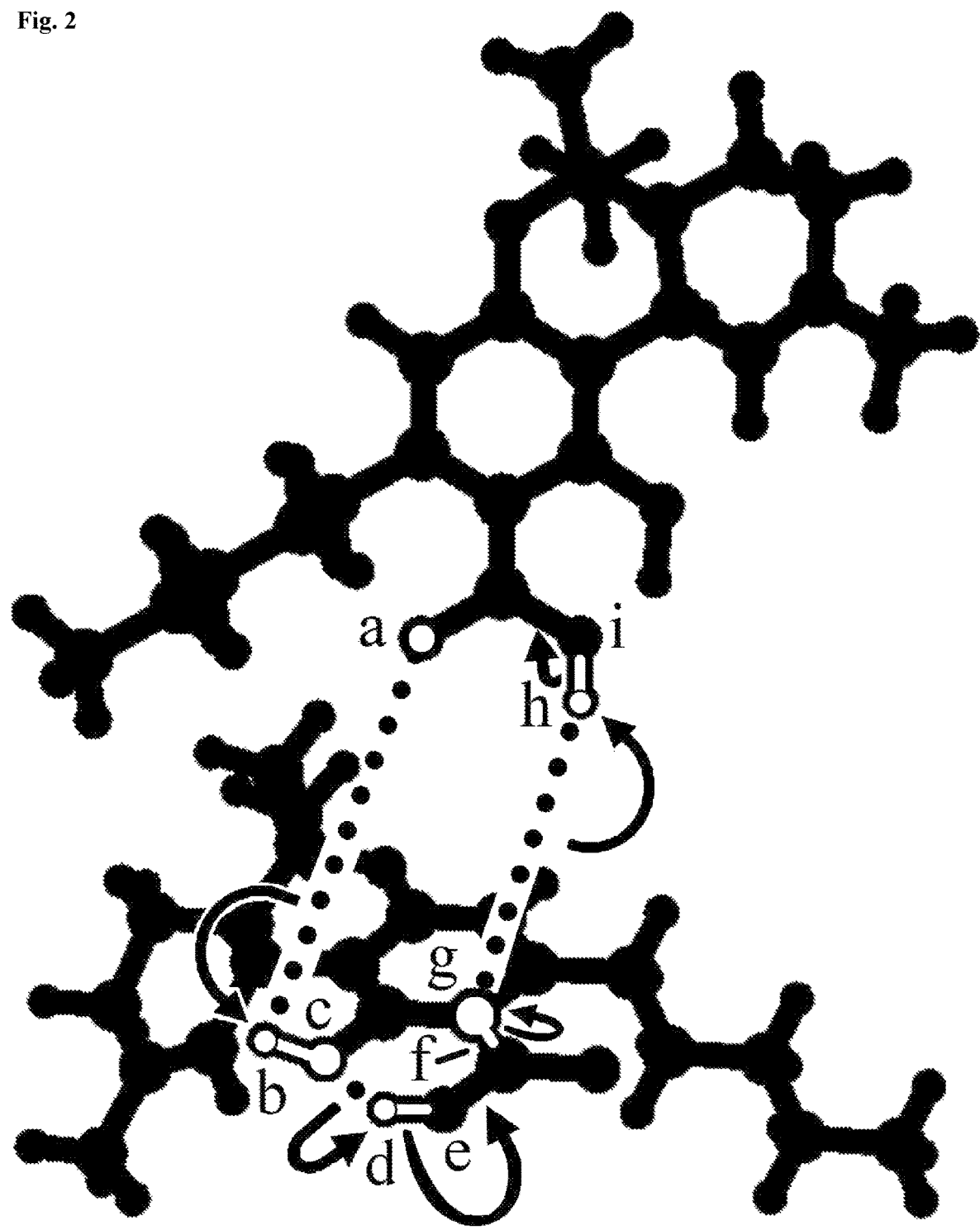
FIG. 2 is a two-dimensional rendering of ball and stick models of two THCA molecules, which depicts two intermolecular hydrogen bonds between the two THCA molecules and electron pair arrow pushing to show a predicted, single-step, cyclic chemical reaction catalyzed by a first THCA molecule that results in the decarboxylation of a second THCA molecule.

FIG. 2 shows a first (6aR,10aR)-1-hydroxy-6,6,9-trimethyl-3-pentyl-6a,7,8,10a-tetrahydro-6H-benzo[c] chromene-2-carboxylic acid ("tetrahydrocannabinolic acid"; "THCA") molecule (FIG. 2, top) catalyzing the decarboxylation of a second THCA molecule (FIG. 2, bottom). Immediately prior to the reaction, the first and second THCA molecules form two intermolecular hydrogen bonds denoted by two long dotted lines in FIG. 2. The hydrogen bond depicted by the left-most dotted line is between an electron pair of the carbonyl oxygen of the first THCA molecule (FIG. 2, "a") and the hydroxyl proton of the second THCA molecule (FIG. 2, "b"). The hydrogen bond depicted by the right-most dotted is between the pi electron cloud of the second THCA molecule (FIG. 2, "g") and the carboxylic acid proton of the first THCA molecule (FIG. 2, "h"). An intramolecular hydrogen bond also forms between an electron pair of the hydroxyl oxygen of the second THCA molecule (FIG. 2, "c") and the carboxylic acid proton of the second THCA molecule (FIG. 2, "d").

The predicted, single-step, cyclic reaction shown in FIG. 2 proceeds by converting the three hydrogen bonds into covalent bonds, breaking four single bonds, converting two single bonds into double bonds, and converting a double bond into a single bond. The hydrogen bond between an electron pair of the carbonyl oxygen of the first THCA molecule (FIG. 2, "a") and the hydroxyl proton of the second THCA molecule (FIG. 2, "b") becomes a covalent bond, which converts the double bond between the carbonyl oxygen (FIG. 2, "a") and carbonyl carbon of the first THCA molecule into a single bond. The hydroxyl of the second THCA molecule reforms by converting the hydrogen bond between an electron pair of the hydroxyl oxygen of the second THCA molecule (FIG. 2, "c") and the carboxylic acid proton of the second THCA molecule (FIG. 2, "d") into a covalent bond. The extra electron pair of the deprotonated carboxylate oxygen of the second THCA molecule (FIG. 2, "e") converts the single bond of the deprotonated carboxylate into a double bond, and the electron pair of the carbon-carbon single bond at the 2-position of the 6H-benzo[c] chromene of the second THCA molecule (FIG. 2, "f") enters the pi electron cloud of the aromatic ring of the second THCA molecule (FIG. 2, "g") to release the deprotonated carboxylate from the second THCA molecule as a carbon dioxide molecule. The hydrogen bond between the pi electron cloud of the second THCA molecule (FIG. 2, "g") and the carboxylic acid proton of the first THCA molecule (FIG. 2, "h") becomes a covalent bond to replace the deprotonated carboxylate at the 2-position of the 6H-benzo[c]chromene of the second THCA molecule (which left the second THCA molecule as a carbon dioxide molecule) with the proton and form a THC molecule. The extra electron pair of the deprotonated oxygen of the first THCA molecule (FIG. 2, "i") converts the single bond between the deprotonated oxygen and carbonyl carbon into a double bond to reform the carboxylic acid of the first THCA molecule.

The reaction mechanism described above is represented by arrows in FIG. 2, which depict electron pair pushing. Atoms that form hydrogen bonds that become covalent bonds are shown with white fill in FIG. 2. Covalent bonds that break are shown with white fill in FIG. 2. Three hydrogen bonds that become covalent bonds are shown with dotted lines in FIG. 2. Specific atoms are annotated by the lowercase letters "a"-"e," "h", and "i" in FIG. 2 as described above. The bond that breaks to decarboxylate the second THCA molecule and release a carbon dioxide molecule is annotated by the lowercase letter "f" in FIG. 2 as described above. The pi electron cloud of the aromatic ring of the second THCA molecule is annotated by the lowercase letter "g" in FIG. 2 as described above.

The reaction mechanisms set forth above are descriptive approximations that conform with classical theories of organic chemistry. Other scientific theories such as quantum mechanical theory might describe the same chemical reaction differently and in a manner that contradicts the reaction mechanism set forth above. Regardless of the precise decarboxylation reaction mechanism, two insights obtained from the reaction mechanism are relevant: (1) a molecule having a functional group that is both a Brønsted acid and a Brønsted base (such as a carboxylic acid) can catalyze the decarboxylation of a cannabinoid, and (2) the accessible orientations between a cannabinoid and a catalyst affect the decarboxylation reaction rate.

An implication of the insights set forth above is that the activation energy of the cannabinoid decarboxylation reaction can be lowered by increasing the probability that a catalyst will contact a cannabinoid at an appropriate geometry to form two intermolecular hydrogen bonds between the catalyst and the cannabinoid. During self-catalysis in the liquid phase, cannabinoids preferentially form roughly-parallel pi-stacking interactions that inhibit the formation of intermolecular hydrogen bonds having geometries capable of the cyclic decarboxylation reaction described above. Conventional decarboxylation by heating liquid cannabinoids partially disrupts the pi-stacking interactions and introduces entropy, which each increase the probability that intermolecular hydrogen bonds will form that have an appropriate geometry and connectivity for the decarboxylation reaction. It has now been discovered that the activation energy can be lowered by introducing entropy into the system by performing the decarboxylation reaction in a gas phase.

Smoking and vaporizing marijuana are both known to decarboxylate cannabinoids, but smoking and vaporizing marijuana are not known to result in near-stoichiometric yields. Smoking degrades a substantial portion of cannabinoids by combustion, thermal oxidation, pyrolysis, and isomerization. Vaporization minimizes combustion, but vaporization nevertheless results in oxidation, pyrolysis, and isomerization.

Laboratory analyses suggest that commercially-available personal vaporizers are capable of variable decarboxylation efficiencies ranging from about 80% efficiency to near-complete decarboxylation when operated under laboratory conditions, but personal vaporizers generate substantial amounts of undesirable side products such as CBN. Consumers compensate for variable decarboxylation efficiency, oxidation, pyrolysis, and isomerization by simply titrating their dose. The laboratory analyses of consumer products that generate a vapor are informative, but these products are less relevant to commercial strategies to produce high-value liquid cannabinoids.

Attempts to decarboxylate cannabinoids by vaporization in industrial processes have met with limited success. The art discloses methods to decarboxylate cannabinoids from plant material by vaporization at a temperature of 145 degrees Celsius for about 30 minutes, which resulted in a purported 95% decarboxylation efficiency (U.S. Patent Application Publication No. 2016/0038437 A1). Actual yields relative to the amounts of cannabinoids in the starting materials were not reported. These methods were also incapable of recovering high yields of decarboxylated cannabinoids without converting a substantial portion of the cannabinoids into undesirable degradation products such as CBN (U.S. Patent Application Publication No. 2016/0038437 A1 at pages 10-11, paragraphs [0141]-[0147]). The recovered cannabinoids included 5.6-14.1% CBN. Formulations comprising CBN at concentrations of 1% or greater as a percentage of total cannabinoids are typically useful only as sleep aids, and concentrations of 5% or greater cause extreme drowsiness. The purification of pharmacologically-relevant cannabinoids from CBN is challenging and limits the usefulness of methods that generate more than 1% CBN as a percentage of total cannabinoids.

The inventors previously developed systems to extract cannabinoids by vaporization (for example, PCT Patent Application Publication No. WO 2015/049585 A2 and WO 2018/102711 A1).

Vaporization generally requires high temperatures, which favor both undesirable pyrolysis and decarboxylation (i.e., desirable pyrolysis). The inventors previously disclosed methods that minimize or eliminate pyrolysis, which minimizes or eliminates decarboxylation by definition (for example, PCT Patent Application Publication No. WO 2015/049585 A2 and WO 2018/102711 A1).

The inventors have now identified methods to decouple decarboxylation from undesirable chemical reactions. The inventors discovered that increasing energy transfer during gas phase decarboxylation surprisingly increases the rate of the decarboxylation reaction without significantly increasing the rate of undesirable oxidation, pyrolysis, and isomerization, which can (1) reduce the time of the decarboxylation reaction from hours to seconds, (2) reduce the energy required for decarboxylation, (3) increase the quality of cannabinoid products, (4) minimize post-decarboxylation clean-up and purification steps, and (5) reduce cost. This conceptual framework allows minimization of both the time and energy required to decarboxylate cannabinoids. The conceptual framework similarly allows optimization of the power required to decarboxylate cannabinoids.

Various aspects of the disclosure relate to a method to chemically modify a cannabinoid molecule. In preferred embodiments, a chemical modification is a decarboxylation of a cannabinoid carboxylic acid or a cannabinoid carboxylate. In some specific embodiments, a chemical modification is the conversion of either cannabidiolic acid or cannabidiolate into cannabidiol. In some specific embodiments, a chemical modification is the conversion of either cannabidivarin carboxylic acid ("CBDVA") or cannabidivarin carboxylate into cannabidivarin ("CBDV"). In some specific embodiments, a chemical modification is the conversion of either tetrahydrocannabinolic acid or tetrahydrocannabinolate into tetrahydrocannabinol. In some specific embodiments, a chemical modification is the conversion of either tetrahydrocannabivarin carboxylic acid ("THCVA") or tetrahydrocannabivarin carboxylate into tetrahydrocannabivarin ("THCV"). In some specific embodiments, a chemical modification is the conversion of either perrottetinenic acid or the conjugate base of perrottetinenic acid into perrottetinene.

The term "molecule," as used in this patent document without further context, refers to either an individual molecule or molecules of a specified type. The term "composition comprising a native cannabinoid molecule," without further context, for example, can optionally refer to either a composition comprising a single native cannabinoid molecule or a composition comprising an amount of a native cannabinoid molecule. Each instance of the term "molecule" in this patent document can be supplemented with the word "single" or the phrase "an amount of" if allowable by context, for example, as shown in the preceding sentence.

In preferred embodiments, a method comprises providing a composition comprising cannabinoids, in which the cannabinoids comprise a native cannabinoid molecule, the native cannabinoid molecule comprises a carboxyl group, and the native cannabinoid molecule is in a liquid phase or a solid phase in the composition. The term "providing" includes, for example, introducing a composition into a system that performs all or part of a method described in this patent document. The term "carboxyl group" refers to either a carboxylic acid group or a carboxylate group.

In preferred embodiments, a method comprises contacting a composition with sufficient energy to convert a native cannabinoid molecule of the composition into (i) a carbon dioxide molecule and (ii) a modified cannabinoid molecule in a gas phase.

In preferred embodiments, a method comprises contacting a modified cannabinoid molecule with a heat sink to condense the modified cannabinoid molecule into a condensed cannabinoid molecule in a liquid distillate.

In preferred embodiments, a method comprises collecting a liquid distillate.

In some embodiments, a composition comprises a plant material. In some specific embodiments, a composition comprises a plant material, and the plant material comprises a native cannabinoid molecule. In some specific embodiments, a composition comprises a ground plant material. In some embodiments, a composition has a surface-area-to-volume ratio greater than 1000 per meter. In specific some embodiments, a composition has a surface-area-to-volume ratio greater than 5000 per meter. Surface-area-to-volume ratios greater than 1000 per meter have greater rates of energy transfer than surface-area-to-volume ratios less than 1000 per meter.

In some embodiments, a plant material is a species of the genus *Cannabis*. In some specific embodiments, a plant material is *Cannabis sativa*. In some specific embodiments, a plant material is *Cannabis indica*. In some specific embodiments, a plant material is *Cannabis ruderalis*. In some very specific embodiments, a plant material is *Cannabis sativa* forma *indica*. In some specific embodiments, a plant material lacks THC and potential THC at a combined concentration greater than 0.3% by weight. A weight of "potential THC" is determined by multiplying the weight of THCA by 314.47 (the molecular weight of THC) and dividing by 358.48 (the molecular weight of THCA). A plant material that contains undetectable THC and 0.33% THCA, for example, contains THC and potential THC at a combined concentration of 0.29% by weight.

In some embodiments, a composition comprises water at a concentration of less than 10% by weight. Water can absorb a large amount of energy by evaporation, and thus, minimizing the water of a composition increases the rate of energy transfer to native cannabinoid molecules.

In some embodiments, a composition comprises an extracted oil that was extracted from a plant material of the genus *Cannabis*. In some specific embodiments, a composition comprises an extracted oil that was extracted from industrial hemp. In some specific embodiments, a composition comprises an extracted oil that was extracted from marijuana.

In some embodiments, a composition comprises a native cannabinoid molecule that was previously extracted from a plant material of the genus *Cannabis*. In some specific embodiments, a composition comprises a native cannabinoid molecule that was previously extracted from industrial hemp. In some specific embodiments, a composition comprises a native cannabinoid molecule that was previously extracted from marijuana.

In some embodiments, a composition comprises industrial hemp or a composition is derived from industrial hemp. In some embodiments, a composition comprises marijuana or a composition is derived from marijuana.

In some specific embodiments, a composition is a liquid. In some very specific embodiments, a composition is an oil. In some specific embodiments, a composition is an aerosol. In some specific embodiments, a composition comprises a suspension of solid particles in a gas. In some specific embodiments, a composition comprises a suspension of liquid droplets in a gas. In some specific embodiments, a composition comprises a powder. In some specific embodiments, a composition comprises crystals. In some specific embodiments, a composition comprises wax.

In some embodiments, a method comprises grinding plant material. In some embodiments, a method comprises separating particles of industrial hemp, marijuana, or other plant material by size such as by using a screen, mesh, or particle classifier.

In preferred embodiments, a native cannabinoid molecule is selected from one or more of THCA, THCVA, tetrahydrocannabiorcolic acid ("THCOA"), CBDA, CBDVA, cannabidiorcolic acid ("CBDOA"), cannabichromenic acid ("CBCA"), cannabichromevarinic acid ("CBCVA"), cannabigerolic acid ("CBGA"), cannabigerovarinic acid ("CBGVA"), cannabicyclolic acid ("CBLA"), cannabielsoic acid ("CBEA"), perrottetinenic acid, one or more carboxylates of any of the preceding molecules, one or more naturally-occurring ethers of any of the preceding molecules, and one or more stereoisomers of any of the preceding molecules.

In preferred embodiments, a modified cannabinoid molecule and a condensed cannabinoid molecule are selected from one or more of THC, THCV, tetrahydrocannabiorcol ("THCO"), CBD, CBDV, cannabidiorcol, ("CBDO"), cannabichromene ("CBC"), cannabichromevarin ("CBCV"), CBG, cannabigerovarin ("CBGV"), cannabicyclol ("CBL"), cannabielsoin ("CBE"), perrottetinene, one or more naturally-occurring ethers of any of the preceding molecules, and one or more stereoisomers of any of the preceding molecules.

In some specific embodiments, a native cannabinoid molecule is THCA, a modified cannabinoid molecule is THC, and a condensed cannabinoid molecule is THC.

In some specific embodiments, a native cannabinoid molecule is THCVA, a modified cannabinoid molecule is THCV, and a condensed cannabinoid molecule is THCV.

In some specific embodiments, a native cannabinoid molecule is THCOA, a modified cannabinoid molecule is THCO, and a condensed cannabinoid molecule is THCO.

In some specific embodiments, a native cannabinoid molecule is CBDA, a modified cannabinoid molecule is CBD, and a condensed cannabinoid molecule is CBD.

In some specific embodiments, a native cannabinoid molecule is CBDVA, a modified cannabinoid molecule is CBDV, and a condensed cannabinoid molecule is CBDV.

In some specific embodiments, a native cannabinoid molecule is CBDOA, a modified cannabinoid molecule is CBDO, and a condensed cannabinoid molecule is CBDO.

In some specific embodiments, a native cannabinoid molecule is CBCA, a modified cannabinoid molecule is CBC, and a condensed cannabinoid molecule is CBC.

In some specific embodiments, a native cannabinoid molecule is CBCVA, a modified cannabinoid molecule is CBCV, and a condensed cannabinoid molecule is CBCV.

In some specific embodiments, a native cannabinoid molecule is CBGA, a modified cannabinoid molecule is CBG, and a condensed cannabinoid molecule is CBG.

In some specific embodiments, a native cannabinoid molecule is CBGVA, a modified cannabinoid molecule is CBGV, and a condensed cannabinoid molecule is CBGV.

In some specific embodiments, a native cannabinoid molecule is CBLA, a modified cannabinoid molecule is CBL, and a condensed cannabinoid molecule is CBL.

In some specific embodiments, a native cannabinoid molecule is CBEA, a modified cannabinoid molecule is CBE, and a condensed cannabinoid molecule is CBE.

In some specific embodiments, a native cannabinoid molecule is perrottetinenic acid, a modified cannabinoid molecule is perrottetinene, and a condensed cannabinoid molecule is perrottetinene.

In some embodiments, a composition comprises a plurality of cannabinoids, and at least 95% of the cannabinoids of the plurality of cannabinoids comprise a carboxyl group.

In some embodiments, a composition comprises a native cannabinoid molecule at a concentration of at least 3% by weight. In some specific embodiments, a composition comprises a native cannabinoid molecule at a concentration by weight of 1% to 10%, 5% to 15%, 10% to 20%, 15% to 25%, 20% to 30%, or 25% to 35%. In some specific embodiments, a composition comprises CBDA, CBDVA, THCA, THCVA, CBCA, and CBGA at a combined concentration of at least 3% by weight. In some very specific embodiments, a composition comprises CBDA, CBDVA, THCA, THCVA, CBCA, and CBGA at a combined concentration by weight of 1% to 10%, 5% to 15%, 10% to 20%, 15% to 25%, 20% to 30%, or 25% to 35%. In some very specific embodiments, a composition comprises CBDA at a concentration of at least 3% by weight. In some very specific embodiments, a composition comprises CBDA at a concentration by weight of 1% to 10%, 5% to 15%, 10% to 20%, 15% to 25%, 20% to 30%, or 25% to 35%. In some very specific embodiments, a composition comprises CBDVA at a concentration of at least 0.1% by weight. In some very specific embodiments, a composition comprises CBDVA at a concentration by weight of 0.1% to 10%, 5% to 15%, 10% to 20%, 15% to 25%, 20% to 30%, or 25% to 35%. In some very specific embodiments, a composition comprises THCA at a concentration of at least 20% by weight. In some very specific embodiments, a composition comprises THCA at a concentration by weight of 10% to 20%, 15% to 25%, 20% to 30%, or 25% to 35%. In some very specific embodiments, a composition comprises THCVA at a concentration of at least 1% by weight. In some very specific embodiments, a composition comprises THCVA at a concentration by weight of 0.1% to 10%, 5% to 15%, 10% to 20%, 15% to 25%, 20% to 30%, or 25% to 35%.

In some embodiments, a method comprises suspending a particle of a composition comprising cannabinoids in a gas phase, in which the particle comprises a native cannabinoid molecule. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a particle of the composition comprising the native cannabinoid molecule is suspended in the gas phase.

In some embodiments, a method comprises suspending a plurality of particles of a composition comprising cannabinoids in a gas phase, in which the plurality of particles comprises a native cannabinoid molecule. In some specific embodiments, a method comprises suspending at least 50% of a composition comprising a native cannabinoid molecule in a gas phase as a plurality of particles. In some very specific embodiments, a method comprises suspending at least 90% of a composition comprising a native cannabinoid molecule in a gas phase as a plurality of particles. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a plurality of particles of the composition comprising the native cannabinoid molecule is suspended in the gas phase.

In some embodiments, a method comprises suspending a droplet of a composition comprising cannabinoids in a gas phase, in which the droplet comprises a native cannabinoid molecule. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a droplet of the composition comprising the native cannabinoid molecule is suspended in the gas phase.

In some embodiments, a method comprises suspending a plurality of droplets of a composition comprising cannabinoids in a gas phase, in which the plurality of droplets comprises a native cannabinoid molecule. In some specific embodiments, a method comprises suspending at least 50% of a composition comprising a native cannabinoid molecule in a gas phase as a plurality of droplets. In some very specific embodiments, a method comprises suspending at least 90% of a composition comprising a native cannabinoid molecule in a gas phase as a plurality of droplets. In some specific embodiments, a composition comprising a native cannabinoid molecule is contacted with sufficient energy to convert the native cannabinoid molecule into (i) a carbon dioxide molecule and (ii) a modified cannabinoid molecule in a gas phase while a plurality of droplets of the composition comprising the native cannabinoid molecule is suspended in the gas phase.

In some embodiments, a gas phase comprises water vapor at a concentration of at least 5% by volume. In some embodiments, a gas phase comprises ethanol vapor at a concentration of at least 5% by volume. In some embodiments, a gas phase comprises molecular nitrogen, ethanol vapor, water vapor, carbon dioxide, noble gases, cannabinoids, terpenes, terpene alcohols, and terpenoids at a combined concentration of at least 90% by volume. In some specific embodiments, a gas phase comprises molecular nitrogen, ethanol vapor, water vapor, carbon dioxide, noble gases, cannabinoids, terpenes, terpene alcohols, and terpenoids at a combined concentration of at least 95% by volume. A gas phase can optionally contain a suspended liquid (such as a droplet or a plurality of droplets), a suspended solid (such as a particle or a plurality of particles), or both a suspended liquid and a suspended solid, and neither a suspended liquid nor a suspended solid is included in a percent-by-volume calculation.

In preferred embodiments, contacting a composition with sufficient energy to convert a native cannabinoid molecule into (i) a carbon dioxide molecule and (ii) a modified cannabinoid molecule in a gas phase comprises contacting the composition with less than 0.04 kilowatt hours of energy per gram of the composition. In some specific embodiments, contacting a composition with sufficient energy to convert a native cannabinoid molecule into (i) a carbon dioxide molecule and (ii) a modified cannabinoid molecule in a gas phase comprises contacting the composition with 0.0004 to 0.04 kilowatt hours of energy per gram of the composition. In some specific embodiments, contacting a composition with sufficient energy to convert a native cannabinoid molecule into (i) a carbon dioxide molecule and (ii) a modified cannabinoid molecule in a gas phase comprises contacting the composition with less than 0.004 kilowatt hours of energy per gram of the composition. In some very specific embodiments, contacting a composition with sufficient energy to convert a native cannabinoid molecule into (i) a carbon dioxide molecule and (ii) a modified cannabinoid molecule in a gas phase comprises contacting the composition with 0.0004 to 0.004 kilowatt hours of energy per gram of the composition.

In some embodiments, contacting a composition with sufficient energy to convert a native cannabinoid molecule into (i) a carbon dioxide molecule and (ii) a modified cannabinoid molecule in a gas phase comprises contacting the composition with energy at a rate of less than 100 kilowatts of power per gram of the composition for a duration of less than 60 seconds. In some specific embodiments, contacting a composition with sufficient energy to convert a native cannabinoid molecule into (i) a carbon dioxide molecule and (ii) a modified cannabinoid molecule in a gas phase comprises contacting the composition with 10 watts to 100 kilowatts of power per gram of the composition for 200 milliseconds to 20 seconds. In some very specific embodiments, contacting a composition with sufficient energy to convert a native cannabinoid molecule into (i) a carbon dioxide molecule and (ii) a modified cannabinoid molecule in a gas phase comprises contacting the composition with 1 to 100 kilowatts of power per gram of the composition for 200 milliseconds to 20 seconds.

In preferred embodiments, a method comprises irradiating a composition, convectively heating a composition, or conductively heating a composition, in which contacting a composition with sufficient energy comprises one or more of irradiating the composition, convectively heating the composition, and conductively heating the composition. Suitable non-limiting methods of irradiating a composition are described, for example, in PCT Patent Application Publication No. WO 2018/102711 A1, which is incorporated by reference in its entirety. Suitable non-limiting methods of convectively heating a composition are described, for example, in PCT Patent Application Publication No. WO 2015/049585 A2, which is incorporated by reference in its entirety. Suitable non-limiting methods of conductively heating a composition are described, for example, in PCT Patent Application Publication No. WO 2016/161420 A1 and WO 2017/192527 A1, each of which is incorporated by reference in its entirety.

In some embodiments, a method comprises contacting a composition with a heated gas. In some specific embodiments, a method comprises contacting a composition with a heated gas having a temperature of 190 to 250 degrees Celsius. In some embodiments, a method comprises contacting a composition with a heated surface. In some specific embodiments, a method comprises contacting a composition with a heated surface having a temperature of 190 to 250 degrees Celsius.

In some embodiments, a composition is contacted with sufficient energy to convert a native cannabinoid molecule of the composition into (i) a carbon dioxide molecule and (ii) a modified cannabinoid molecule in a gas phase under vacuum. In some specific embodiments, a composition is contacted with sufficient energy to convert a native cannabinoid molecule of the composition into (i) a carbon dioxide molecule and (ii) a modified cannabinoid molecule in a gas phase at a pressure of 100 pascals to 100 kilopascals. In some very specific embodiments, a composition is contacted with sufficient energy to convert a native cannabinoid molecule of the composition into (i) a carbon dioxide molecule and (ii) a modified cannabinoid molecule in a gas phase at a pressure of 900 pascals to 90 kilopascals. Reducing pressure can increase entropy by partitioning molecules into the gas phase.

In some embodiments, a composition is contacted with sufficient energy to convert a native cannabinoid molecule of the composition into (i) a carbon dioxide molecule and (ii) a modified cannabinoid molecule in a gas phase at about atmospheric pressure. In some embodiments, a composition is contacted with sufficient energy to convert a native cannabinoid molecule of the composition into (i) a carbon dioxide molecule and (ii) a modified cannabinoid molecule in a gas phase at a pressure greater than atmospheric pressure.

In some embodiments, a method comprises directing a composition comprising cannabinoids along a path having a length of at least 4 meters, in which the composition is contacted with sufficient energy to convert a native cannabinoid molecule of the composition into (i) a carbon dioxide molecule and (ii) a modified cannabinoid molecule in a gas phase while the composition is being directed along the path. In some specific embodiments, a method comprises directing a composition comprising cannabinoids along a path having a length of 5 meters to 20 meters, in which the composition is contacted with sufficient energy to convert a native cannabinoid molecule of the composition into (i) a carbon dioxide molecule and (ii) a modified cannabinoid molecule in a gas phase while the composition is being directed along the path. Increasing the length of a path increases the probability that a first native cannabinoid molecule will interact with either a second native cannabinoid molecule or other catalyst with an appropriate orientation to catalyze the decarboxylation of the first native cannabinoid molecule. In some specific embodiments, a path is a heated path.

In some embodiments, a method comprises directing a composition along a path having a length of at least 4 meters at a rate of at least 2 meters per second. Directing a composition along a path of a specific length at a specific rate can control the amount of energy that contacts the composition.

In some embodiments, a path comprises one or more surfaces, and a method comprises heating the one or more surfaces to a temperature of 190 to 250 degrees Celsius.

In some embodiments, a composition comprises a non-volatile molecule, and a method comprises separating a modified cannabinoid molecule in a gas phase from the non-volatile molecule, in which the non-volatile molecule is suspended in the gas phase. In some specific embodiments, separating a modified cannabinoid molecule in a gas phase from a non-volatile molecule is performed after converting a native cannabinoid molecule into (i) a carbon dioxide molecule and (ii) the modified cannabinoid molecule in the gas phase. In some specific embodiments, separating a modified cannabinoid molecule in a gas phase from a non-volatile molecule is performed prior to contacting the modified cannabinoid molecule with a heat sink. In some very specific embodiments, a method comprises separating a modified cannabinoid molecule in a gas phase from a non-volatile molecule by directing the gas phase through a cyclone. In some very specific embodiments, a method comprises separating a modified cannabinoid molecule in a gas phase from a non-volatile molecule by directing the gas phase through a filter such as an air filter. In some specific embodiments, a method comprises collecting a non-volatile molecule. Non-volatile molecules optionally include one or more of chlorophyll, cellulose, nucleic acids, proteins, carbohydrates, sugars, triglycerides, phospholipids, fatty acids, salts, ions, ash, glass, sand, rock, metal, polymers, and certain microwave-absorbing agents (described, for example, in PCT Patent Application Publication No. WO 2018/102711 A1).

In some embodiments, a method converts less than 2% of a native cannabinoid molecule of a composition into CBN by mole. In some specific embodiments, a method comprises producing a liquid distillate comprising a condensed cannabinoid molecule and CBN at a molar ratio greater than 100:1. In some specific embodiments, a composition comprises one or both of CBDA and CBD, and a method converts less than 2% of the CBDA and CBD of the composition into CBN by mole. In some very specific embodiments, a method comprises producing a liquid distillate comprising CBD and CBN at a molar ratio greater than 100:1. In some specific embodiments, a composition comprises one or both of THCA and THC, and a method converts less than 2% of the THCA and THC of the composition into CBN by mole. In some very specific embodiments, a method comprises producing a liquid distillate comprising THC and CBN at a molar ratio greater than 100:1.

In some embodiments, a method converts less than 0.2% of a native cannabinoid molecule of a composition into delta-8-tetrahydrocannabinol ("delta-8-THC") by mole. In some specific embodiments, a method comprises producing a liquid distillate comprising a condensed cannabinoid molecule and delta-8-THC at a molar ratio greater than 300:1. In some specific embodiments, a composition comprises one or both of CBDA and CBD, and a method converts less than 0.2% of the CBDA and CBD of the composition into delta-8-THC by mole. In some very specific embodiments, a method comprises producing a liquid distillate comprising CBD and delta-8-THC at a molar ratio greater than 300:1. In some specific embodiments, a composition comprises one of both of THCA and THC, and a method converts less than 0.2% of the THCA and THC of the composition into delta-8-THC by mole. In some very specific embodiments, a method comprises producing a liquid distillate comprising THC and delta-8-THC at a molar ratio greater than 300:1.

In some specific embodiments, a method converts less than 2% of a native cannabinoid molecule of a composition into CBN by mole. In some very specific embodiments, a composition comprises a native cannabinoid molecule, the native cannabinoid molecule is CBDA, and a method converts less than 2% of the CBDA into CBN by mole. In some very specific embodiments, a composition comprises a native cannabinoid molecule, the native cannabinoid molecule is THCA, and a method converts less than 2% of the THCA into CBN by mole.

In some specific embodiments, a method converts less than 0.2% of a native cannabinoid molecule into delta-8-THC by mole. In some very specific embodiments, a composition comprises a native cannabinoid molecule, the native cannabinoid molecule is CBDA, and a method converts less than 0.2% of the CBDA into delta-8-THC by mole. In some very specific embodiments, a composition comprises a native cannabinoid molecule, the native cannabinoid molecule is THCA, and a method converts less than 0.2% of the THCA into delta-8-THC by mole.

In some embodiments, a heat sink has a surface area greater than 10% of the surface area of a composition comprising cannabinoids. A heat sink having a relatively large surface area allows for rapid condensation. In some specific embodiments, a heat sink is a colloid comprising a gas-phase dispersion medium. In some very specific embodiments, a heat sink is an aerosol or a foam. In some very specific embodiments, a heat sink is a spray. Colloids such as aerosols and foams generally have large surface areas, and colloids are therefore suitable heat sinks.

In some embodiments, a heat sink comprises a volatile liquid. Heat sinks comprising a volatile liquid are particularly useful because the vaporization of a volatile liquid can absorb a large amount of energy. In some specific embodiments, a heat sink comprises a volatile liquid, and the volatile liquid comprises one or both of ethanol and water. In some very specific embodiments, a heat sink comprises a volatile liquid, and the volatile liquid comprises ethanol and water at a combined concentration by weight of at least 90%.

In some embodiments, contacting a modified cannabinoid molecule with a heat sink comprises passive cooling such as by exposing the modified cannabinoid molecule or a container comprising the modified cannabinoid molecule to ambient temperature. In some specific embodiments, exposing a modified cannabinoid molecule or a container comprising the modified cannabinoid molecule to ambient temperature comprises cooling in an autoclave.

In some embodiments, contacting a modified cannabinoid molecule with a heat sink comprises directing the modified cannabinoid molecule through a fluid-cooled condenser.

In some embodiments, a method comprises contacting a modified cannabinoid molecule with a heat sink less than 240 seconds after contacting a composition with sufficient energy to convert a native cannabinoid molecule into (i) a carbon dioxide molecule and (ii) the modified cannabinoid molecule. In some specific embodiments, a method comprises contacting a modified cannabinoid molecule with a heat sink less than 10 seconds after contacting a composition with sufficient energy to convert a native cannabinoid molecule into (i) a carbon dioxide molecule and (ii) the modified cannabinoid molecule. In preferred embodiments, a method comprises condensing a modified cannabinoid molecule into a condensed cannabinoid molecule less than 240 seconds after contacting a composition with sufficient energy to convert a native cannabinoid molecule into (i) a carbon dioxide molecule and (ii) the modified cannabinoid molecule. In some specific embodiments, a method comprises condensing a modified cannabinoid molecule into a condensed cannabinoid molecule less than 10 seconds after contacting a composition with sufficient energy to convert a native cannabinoid molecule into (i) a carbon dioxide molecule and (ii) the modified cannabinoid molecule.

In some specific embodiments, a method comprises producing a liquid distillate comprising CBN at a concentration less than 0.8% by weight. In some specific embodiments, a method comprises producing a liquid distillate comprising one or both of CBD and THC at a combined concentration greater than 6% by weight and CBN at a concentration less than 0.8% by weight.

In some specific embodiments, a method comprises producing a liquid distillate comprising condensed cannabinoids, in which less than 2% of the condensed cannabinoids of the liquid distillate comprise a carboxyl group. In some specific embodiments, a method comprises converting at least 75% of a native cannabinoid molecule of a composition into a condensed cannabinoid molecule in a liquid distillate by mole.

In preferred embodiments, a method comprises producing a liquid distillate comprising condensed cannabinoid molecules selected from one, two, three, four, five, or each of CBD, CBDV, THC, THCV, CBC, and CBG. In some specific embodiments, a method comprises producing a liquid distillate comprising condensed cannabinoid molecules in which at least 95% of the condensed cannabinoid molecules of the liquid distillate are CBD, CBDV, THC, THCV, CBC, and CBG by weight.

In some embodiments, a method comprises producing a liquid distillate comprising ethanol. In some specific embodiments, a method comprises producing a liquid distillate comprising ethanol at a concentration of at least 50% by weight, in which a condensed cannabinoid molecule is dissolved in the ethanol. Ethanol reduces the viscosity of a liquid distillate, which improves the flow of a liquid distillate in automated systems at lower temperatures.

In some embodiments, a liquid distillate comprises a non-cannabinoid molecule and a condensed cannabinoid molecule, and a method comprises separating the non-cannabinoid molecule from the condensed cannabinoid molecule to produce a product. In some specific embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of at least 55% by weight. In some very specific embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of 55% to 80% by weight. In some very specific embodiments, a liquid distillate comprises a non-cannabinoid molecule and a condensed cannabinoid molecule, and a method comprises separating the non-cannabinoid molecule from the condensed cannabinoid molecule to produce a product comprising the condensed cannabinoid molecule at a concentration of 75% to 99.9% by weight.

In some embodiments, a non-cannabinoid molecule is ethanol. In some embodiments, a non-cannabinoid molecule is a terpene, terpene alcohol, or terpenoid.

In some specific embodiments, a liquid distillate comprises a non-cannabinoid molecule and CBD, and a method comprises separating the non-cannabinoid molecule from the CBD to produce a product comprising the CBD at a concentration of at least 55% by weight. In some very specific embodiments, a liquid distillate comprises a non-cannabinoid molecule and CBD, and a method comprises separating the non-cannabinoid molecule from the CBD to produce a product comprising the CBD at a concentration of 55% to 80% by weight. In some very specific embodiments, a liquid distillate comprises a non-cannabinoid molecule and CBD, and a method comprises separating the non-cannabinoid molecule from the CBD to produce a product comprising the CBD at a concentration of 75% to 99.9% by weight.

In some specific embodiments, a liquid distillate comprises a non-cannabinoid molecule and CBDV, and a method comprises separating the non-cannabinoid molecule from the CBDV to produce a product comprising the CBDV at a concentration of at least 0.7% by weight. In some very specific embodiments, a liquid distillate comprises a non-cannabinoid molecule and CBDV, and a method comprises separating the non-cannabinoid molecule from the CBDV to produce a product comprising the CBDV at a concentration of 0.1% to 10% by weight.

In some specific embodiments, a liquid distillate comprises a non-cannabinoid molecule and THC, and a method comprises separating the non-cannabinoid molecule from the THC to produce a product comprising the THC at a concentration of at least 55% by weight. In some very specific embodiments, a liquid distillate comprises a non-cannabinoid molecule and THC, and a method comprises separating the non-cannabinoid molecule from the THC to produce a product comprising the THC at a concentration of 55% to 80% by weight. In some very specific embodiments, a liquid distillate comprises a non-cannabinoid molecule and THC, and a method comprises separating the non-cannabinoid molecule from the THC to produce a product comprising the THC at a concentration of 75% to 99.9% by weight.

In some specific embodiments, a liquid distillate comprises a non-cannabinoid molecule and THCV, and a method comprises separating the non-cannabinoid molecule from the THCV to produce a product comprising the THCV at a concentration of at least 0.7% by weight. In some very specific embodiments, a liquid distillate comprises a non-cannabinoid molecule and THCV, and a method comprises separating the non-cannabinoid molecule from the THCV to produce a product comprising the THCV at a concentration of 0.1% to 10% by weight.

In some embodiments, a product is a liquid comprising a condensed cannabinoid molecule and at least one solute, in which the condensed cannabinoid molecule is a solvent, and the at least one solute is dissolved in the solvent. In some specific embodiments, a product is a liquid comprising CBD and THC; the CBD is a solvent; the THC is a solute; and the THC is dissolved in the CBD. In some specific embodiments, a product is a liquid comprising THC and CBD; the THC is a solvent; the CBD is a solute; and the CBD is dissolved in the THC.

In some embodiments, a product is a colloid comprising a liquid dispersion medium, in which the liquid dispersion medium comprises a condensed cannabinoid molecule and at least one solute; the condensed cannabinoid molecule is a solvent; and the at least one solute is dissolved in the solvent. In some specific embodiments, a product is a colloid comprising a liquid dispersion medium, in which the liquid dispersion medium comprises CBD and THC; the CBD is a solvent; the THC is a solute; and the THC is dissolved in the CBD. In some specific embodiments, a product is a colloid comprising a liquid dispersion medium, in which the liquid dispersion medium comprises THC and CBD; the THC is a solvent; the CBD is a solute; and the CBD is dissolved in the THC.

Various combinations of the features disclosed in this patent document will be evident to those of ordinary skill, and these combinations are expressly contemplated by the inventors. This patent document discloses each linguistic and grammatical combination of different features disclosed anywhere in the patent document as though any specific combination were disclosed in the same sentence. The language and grammar of this patent document is intentionally selected to explicitly clarify the combinations contemplated by the inventors. All of the embodiments designated as "preferred embodiments" are expressly combinable.

The words "comprising," "comprises," and "comprise" refer to open-ended sets. For example, a composition comprising water can also comprise ethanol.

The phrases "consisting of," "consists of," and "consist of" refer to closed sets. For example, a composition consisting of water cannot also comprise ethanol.

The following examples provide a framework to implement certain aspects of the disclosure, and these examples do not limit the scope of this patent document or any claim that matures from the disclosure of this patent document.

EXEMPLIFICATION

Figure 3:
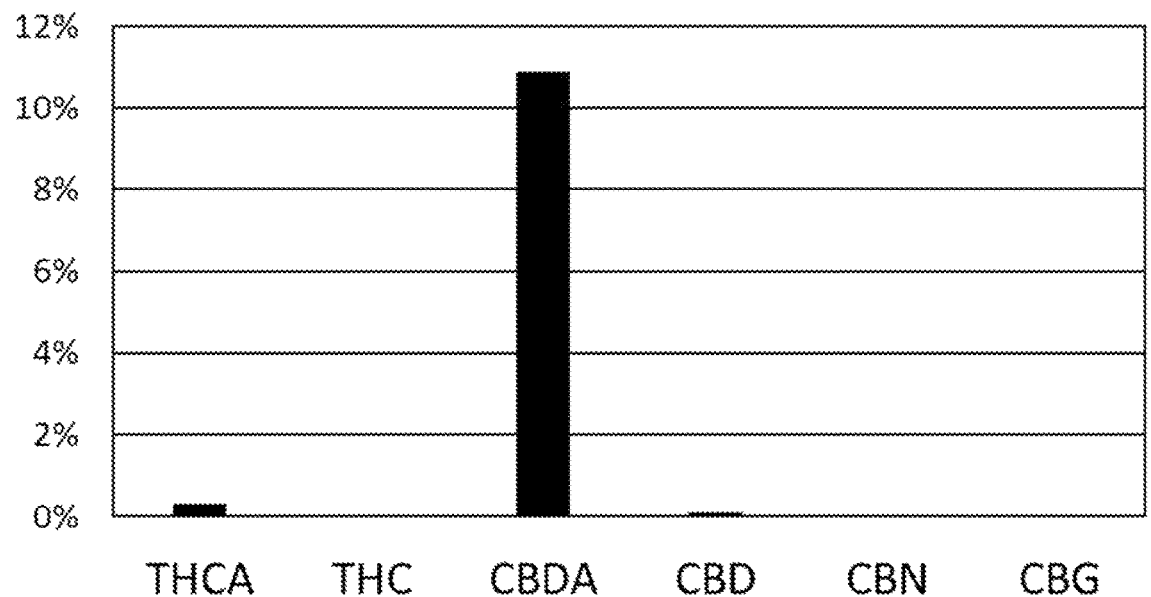
FIG. 3 is a bar graph depicting the THCA, THC, CBDA, CBD, CBN, and cannabigerol ("CBG") concentrations found in a typical sample of USDA organic industrial hemp.

Example 1. Decarboxylation and Extraction of Cannabinoids from Organic Industrial Hemp The method of PCT Patent Application Publication No. WO 2016/161420 A1 is performed using organic industrial hemp and the parameters described in this example. The water content of the hemp is less than 10% by weight. The cannabinoid content of the hemp is about 11-12% by weight and consists of about 11% CBDA, 0.1% CBD, 0.3% THCA, and 0% THC by weight (see, for example, FIG. 3). The hemp is ground and sifted to provide a particulate having a surface-area-to-volume ratio greater than 5000 per meter. The hemp is suspended in heated gas to vaporize the cannabinoids. The heated gas is produced by resistive heating at 10-20 kilowatts. The oxygen content of the heated gas is significantly below the ~20% oxygen content of air by volume. Oxygen is reduced relative to air by evaporating water from the hemp. The heated gas and suspended hemp are directed along a heated path having a length of 5 to 50 meters at a rate of 5 to 20 meters per second. A known mass of hemp is directed along the heated path at a known rate such that the hemp is exposed to less than 0.04 kilowatt hours of energy per gram of the hemp. Cannabinoid vapor is mechanically separated from suspended non-volatile molecules of the hemp including cellulose and chlorophyll using a cyclone and filters. Cannabinoid vapor is condensed by a heat sink less than 10 seconds after vaporization. A liquid distillate is collected by rinsing the condensed cannabinoids from surfaces of the heat sink with ethanol. Greater than 90% of the cannabinoids of the hemp are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

Figure 4:
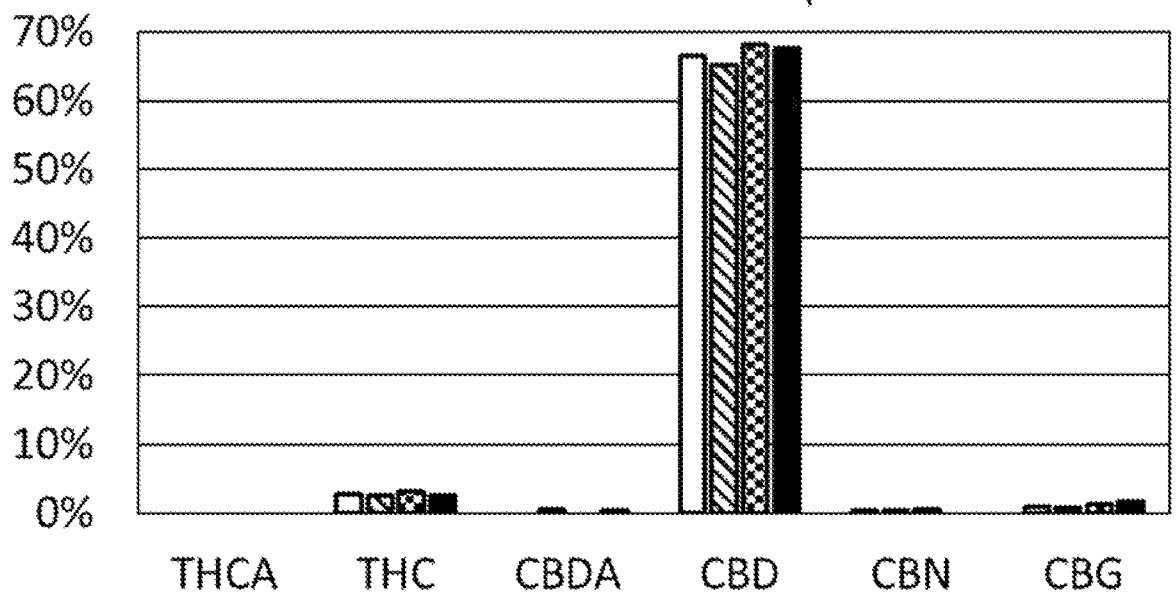
FIG. 4 is a bar graph depicting the THCA, THC, CBDA, CBD, CBN, and CBG concentrations found in four different concentrate products produced according to methods disclosed in this patent document.

Example 2. Products Produced by Decarboxylation and Extraction of Cannabinoids from Organic Industrial Hemp The method of Example 1 was performed on four different batches of organic hemp, and cannabinoid concentrations of concentrated products produced from the liquid distillates were determined by an accredited, third-party *cannabis* testing laboratory. Actual cannabinoid concentrations by weight of concentrated products produced from liquid distillates are shown in FIG. 4 and in Table 1. In each instance, greater than 99% of the cannabinoids of the concentrated products were decarboxylated.

TABLE 1

Actual Concentrations of Cannabinoids in Four Concentrated Products Produced from Liquid Distillate Following Decarboxylation and Extraction of Cannabinoids from Organic Industrial Hemp

|      | 1     | 2     | 3     | 4     |
|------|-------|-------|-------|-------|
| CBD  | 66.5% | 65.2% | 68.1% | 67.6% |
| CBDA | 0.0%  | 0.6%  | 0.0%  | 0.3%  |
| THC  | 2.7%  | 2.6%  | 3.2%  | 2.6%  |
| THCA | 0.0%  | 0.0%  | 0.0%  | 0.0%  |
| CBN  | 0.4%  | 0.3%  | 0.4%  | 0.0%  |
| CBG  | 0.96% | 0.76% | 1.27% | 1.62% |

Example 3. Decarboxylation and Extraction of Cannabinoids from Organic *Cannabis*

The method of PCT Patent Application Publication No. WO 2016/161420 A1 is performed using organic *cannabis* and the parameters described in this example. The water content of the *cannabis* is less than 10% by weight. The cannabinoid content of the *cannabis* is about 20-30% by weight. The *cannabis* is ground and sifted to provide a particulate having a surface-area-to-volume ratio greater than 5000 per meter. The *cannabis* is suspended in heated gas to vaporize the cannabinoids. The heated gas is produced by resistive heating at 10-20 kilowatts. The oxygen content of the heated gas is significantly below the ~20% oxygen content of air by volume. Oxygen is reduced relative to air by evaporating water from the *cannabis*. The heated gas and suspended *cannabis* are directed along a heated path having a length of 5 to 50 meters at a rate of 5 to 20 meters per second. A known mass of *cannabis* is directed along the heated path at a known rate such that the *cannabis* is exposed to less than 0.04 kilowatt hours of energy per gram of the *cannabis*. Cannabinoid vapor is mechanically separated from suspended non-volatile molecules of the *cannabis* including cellulose and chlorophyll using a cyclone and filters. Cannabinoid vapor is condensed by a heat sink less than 10 seconds after vaporization. A liquid distillate is collected by rinsing the condensed cannabinoids from surfaces of the heat sink with ethanol. Greater than 90% of the cannabinoids of the *cannabis* are recovered as cannabinoids of the liquid distillate by mole. Greater than 95% of the cannabinoids of the liquid distillate are decarboxylated. A rotary evaporator is used to remove ethanol and water from the liquid distillate to produce a uniform product comprising at least 10% by weight cannabinoids.

What is claimed is:

1. A method to chemically modify a cannabinoid molecule, comprising:
    providing a composition comprising cannabinoids, wherein the composition comprises an extracted oil that was extracted from a plant material of the genus *Cannabis*, the extracted oil comprises the cannabinoids, the cannabinoids comprise a native cannabinoid molecule, and the native cannabinoid molecule comprises a carboxyl group;
    coating a heated surface with the composition at a surface-area-to-volume ratio of the composition that is greater than 500 per meter;
    contacting the composition with sufficient energy from the heated surface to convert the native cannabinoid molecule into (i) a carbon dioxide molecule and (ii) a modified cannabinoid molecule in a gas phase;
    contacting the modified cannabinoid molecule with a heat sink to condense the modified cannabinoid molecule into a condensed cannabinoid molecule in a liquid distillate; and
    collecting the liquid distillate,
    wherein:
    the method comprises converting less than 2 percent of the native cannabinoid molecule into cannabinol by mole;
    the method is performed such that the liquid distillate comprises the condensed cannabinoid molecule and cannabinol at a molar ratio of greater than 100:1; and
    the method is performed such that the liquid distillate comprises cannabinol at a concentration of less than 0.8 percent by weight.

2. A method to chemically modify a cannabinoid molecule, comprising:
    providing a composition comprising cannabinoids, wherein the composition comprises an extracted oil that was extracted from a plant material of the genus *Cannabis*, the extracted oil comprises the cannabinoids, the cannabinoids comprise a native cannabinoid molecule, and the native cannabinoid molecule comprises a carboxyl group;
    coating a heated surface with the composition at a surface-area-to-volume ratio of the composition that is greater than 500 per meter;
    contacting the composition with sufficient energy from the heated surface to convert the native cannabinoid molecule into (i) a carbon dioxide molecule and (ii) a modified cannabinoid molecule in a gas phase;
    contacting the modified cannabinoid molecule with a heat sink to condense the modified cannabinoid molecule into a condensed cannabinoid molecule in a liquid distillate; and
    collecting the liquid distillate,
    wherein the method is performed such that:
    the liquid distillate comprises the condensed cannabinoid molecule and cannabinol at a molar ratio of greater than 100:1; and
    the liquid distillate comprises the condensed cannabinoid molecule and delta-8-tetrahydrocannabinol at a molar ratio of greater than 300:1.

3. The method of claim 2, wherein:
the native cannabinoid molecule is cannabidiolic acid;
the modified cannabinoid molecule is cannabidiol; and
the condensed cannabinoid molecule is cannabidiol.

4. The method of claim 2, wherein:
the native cannabinoid molecule is tetrahydrocannabinolic acid;
the modified cannabinoid molecule is tetrahydrocannabinol; and
the condensed cannabinoid molecule is tetrahydrocannabinol.

5. The method of claim 4, comprising producing a product comprising tetrahydrocannabinol at a concentration of at least 55 percent by weight from the liquid distillate.

6. The method of claim 4, wherein the sufficient energy is at least 0.0004 kilowatt hours and no greater than 0.04 kilowatt hours of energy per gram of the composition.

7. The method of claim 4, wherein the sufficient energy is at least 0.0004 kilowatt hours and no greater than 0.004 kilowatt hours of energy per gram of the composition.

8. A method to chemically modify a cannabinoid molecule, comprising:
providing a composition comprising cannabinoids, wherein the composition comprises an extracted oil that was extracted from a plant material of the genus *Cannabis*, the extracted oil comprises the cannabinoids, the cannabinoids comprise a native cannabinoid molecule, and the native cannabinoid molecule comprises a carboxyl group;
coating a heated surface with the composition at a surface-area-to-volume ratio of the composition that is greater than 500 per meter;
contacting the composition with sufficient energy from the heated surface to convert the native cannabinoid molecule into (i) a carbon dioxide molecule and (ii) a modified cannabinoid molecule in a gas phase, wherein the gas phase comprises less than 5 percent by volume molecular oxygen;
contacting the modified cannabinoid molecule with a heat sink to condense the modified cannabinoid molecule into a condensed cannabinoid molecule in a liquid distillate; and
collecting the liquid distillate.

9. A method to chemically modify a cannabinoid molecule, comprising:
providing a composition comprising cannabinoids, wherein the composition comprises an extracted oil that was extracted from a plant material of the genus *Cannabis*, the extracted oil comprises the cannabinoids, the cannabinoids comprise a native cannabinoid molecule, and the native cannabinoid molecule comprises a carboxyl group;
coating a heated surface with the composition at a surface-area-to-volume ratio of the composition that is greater than 500 per meter, wherein the heated surface is a surface of a thin-film evaporator;
contacting the composition with sufficient energy from the heated surface to convert the native cannabinoid molecule into (i) a carbon dioxide molecule and (ii) a modified cannabinoid molecule in a gas phase;
contacting the modified cannabinoid molecule with a heat sink to condense the modified cannabinoid molecule into a condensed cannabinoid molecule in a liquid distillate; and
collecting the liquid distillate.

10. A method to chemically modify a cannabinoid molecule, comprising:
providing a composition comprising cannabinoids, wherein the composition comprises an extracted oil that was extracted from a plant material of the genus *Cannabis*, the extracted oil comprises the cannabinoids, the cannabinoids comprise a native cannabinoid molecule, and the native cannabinoid molecule comprises a carboxyl group;
coating a heated surface with the composition at a surface-area-to-volume ratio of the composition that is greater than 500 per meter;
contacting the composition with sufficient energy from the heated surface to convert the native cannabinoid molecule into (i) a carbon dioxide molecule and (ii) a modified cannabinoid molecule in a gas phase wherein the sufficient energy is at least 0.0004 kilowatt hours and no greater than 0.004 kilowatt hours of energy per gram of the composition;
contacting the modified cannabinoid molecule with a heat sink to condense the modified cannabinoid molecule into a condensed cannabinoid molecule in a liquid distillate; and
collecting the liquid distillate.

11. The method of claim 8, wherein:
the native cannabinoid molecule is tetrahydrocannabinolic acid;
the modified cannabinoid molecule is tetrahydrocannabinol;
the condensed cannabinoid molecule is tetrahydrocannabinol; and
the sufficient energy is less than 0.004 kilowatt hours of energy per gram of the composition.

12. The method of claim 8, wherein:
the native cannabinoid molecule is tetrahydrocannabinolic acid;
the modified cannabinoid molecule is tetrahydrocannabinol;
the condensed cannabinoid molecule is tetrahydrocannabinol; and
the sufficient energy is at least 0.0004 kilowatt hours and no greater than 0.004 kilowatt hours of energy per gram of the composition.

13. The method of claim 8, wherein:
the native cannabinoid molecule is tetrahydrocannabinolic acid;
the modified cannabinoid molecule is tetrahydrocannabinol;
the condensed cannabinoid molecule is tetrahydrocannabinol; and
the method is performed such that the liquid distillate comprises the condensed cannabinoid molecule and cannabinol at a molar ratio of greater than 100:1.

14. The method of claim 8, wherein:
the native cannabinoid molecule is tetrahydrocannabinolic acid;
the modified cannabinoid molecule is tetrahydrocannabinol;
the condensed cannabinoid molecule is tetrahydrocannabinol;
the method is performed such that the liquid distillate comprises the condensed cannabinoid molecule and cannabinol at a molar ratio of greater than 100:1; and
the sufficient energy is less than 0.004 kilowatt hours of energy per gram of the composition.

15. The method of claim 8, wherein:
the native cannabinoid molecule is tetrahydrocannabinolic acid;
the modified cannabinoid molecule is tetrahydrocannabinol;
the condensed cannabinoid molecule is tetrahydrocannabinol; and
the method is performed such that the liquid distillate comprises the condensed cannabinoid molecule and delta-8-tetrahydrocannabinol at a molar ratio of greater than 300:1.

16. The method of claim 8, wherein:
the native cannabinoid molecule is tetrahydrocannabinolic acid;
the modified cannabinoid molecule is tetrahydrocannabinol;
the condensed cannabinoid molecule is tetrahydrocannabinol;
the method is performed such that the liquid distillate comprises the condensed cannabinoid molecule and delta-8-tetrahydrocannabinol at a molar ratio of greater than 300:1; and
the sufficient energy is less than 0.004 kilowatt hours of energy per gram of the composition.

17. The method of claim 9, wherein:
the native cannabinoid molecule is tetrahydrocannabinolic acid;
the modified cannabinoid molecule is tetrahydrocannabinol;
the condensed cannabinoid molecule is tetrahydrocannabinol; and
the sufficient energy is less than 0.004 kilowatt hours of energy per gram of the composition.

18. The method of claim 9, wherein:
the native cannabinoid molecule is tetrahydrocannabinolic acid;
the modified cannabinoid molecule is tetrahydrocannabinol;
the condensed cannabinoid molecule is tetrahydrocannabinol; and
the sufficient energy is at least 0.0004 kilowatt hours and no greater than 0.004 kilowatt hours of energy per gram of the composition.

19. The method of claim 9, wherein:
the native cannabinoid molecule is tetrahydrocannabinolic acid;
the modified cannabinoid molecule is tetrahydrocannabinol;
the condensed cannabinoid molecule is tetrahydrocannabinol; and
the method is performed such that the liquid distillate comprises the condensed cannabinoid molecule and cannabinol at a molar ratio of greater than 100:1.

20. The method of claim 9, wherein:
the native cannabinoid molecule is tetrahydrocannabinolic acid;
the modified cannabinoid molecule is tetrahydrocannabinol;
the condensed cannabinoid molecule is tetrahydrocannabinol;
the method is performed such that the liquid distillate comprises the condensed cannabinoid molecule and cannabinol at a molar ratio of greater than 100:1; and
the sufficient energy is less than 0.004 kilowatt hours of energy per gram of the composition.

21. The method of claim 9, wherein:
the native cannabinoid molecule is tetrahydrocannabinolic acid;
the modified cannabinoid molecule is tetrahydrocannabinol;
the condensed cannabinoid molecule is tetrahydrocannabinol; and
the method is performed such that the liquid distillate comprises the condensed cannabinoid molecule and delta-8-tetrahydrocannabinol at a molar ratio of greater than 300:1.

22. The method of claim 9, wherein:
the native cannabinoid molecule is tetrahydrocannabinolic acid;
the modified cannabinoid molecule is tetrahydrocannabinol;
the condensed cannabinoid molecule is tetrahydrocannabinol;
the method is performed such that the liquid distillate comprises the condensed cannabinoid molecule and delta-8-tetrahydrocannabinol at a molar ratio of greater than 300:1; and
the sufficient energy is less than 0.004 kilowatt hours of energy per gram of the composition.

23. A method to chemically modify a cannabinoid molecule, comprising:
providing a composition comprising cannabinoids, wherein the composition comprises an extracted oil that was extracted from a plant material of the genus *Cannabis*, the extracted oil comprises the cannabinoids, the cannabinoids comprise a tetrahydrocannabinolic acid molecule, and the tetrahydrocannabinolic acid molecule comprises a carboxyl group;
coating a heated surface with the composition at a surface-area-to-volume ratio of the composition that is greater than 500 per meter;
contacting the composition with sufficient energy from the heated surface to convert the tetrahydrocannabinolic acid molecule into (i) a carbon dioxide molecule and (ii) a tetrahydrocannabinol molecule in a gas phase, wherein the gas phase comprises less than 5 percent by volume molecular oxygen;
contacting the tetrahydrocannabinol molecule with a heat sink to condense the tetrahydrocannabinol molecule into a condensed tetrahydrocannabinol molecule in a liquid distillate that comprises the condensed tetrahydrocannabinol molecule and cannabinol at a molar ratio of greater than 100:1;
collecting the liquid distillate; and
producing a product comprising tetrahydrocannabinol at a concentration of at least 55 percent by weight from the liquid distillate.

24. A method to chemically modify a cannabinoid molecule, comprising:
providing a composition comprising cannabinoids, wherein the composition comprises an extracted oil that was extracted from a plant material of the genus *Cannabis*, the extracted oil comprises the cannabinoids, the cannabinoids comprise a tetrahydrocannabinolic acid molecule, and the tetrahydrocannabinolic acid molecule comprises a carboxyl group;
coating a heated surface with the composition at a surface-area-to-volume ratio of the composition that is greater than 500 per meter;
contacting the composition with sufficient energy from the heated surface to convert the tetrahydrocannabinolic acid molecule into (i) a carbon dioxide molecule and (ii) a tetrahydrocannabinol molecule in a gas phase, wherein the sufficient energy is less than 0.004 kilowatt hours of energy per gram of the composition, and the gas phase comprises less than 5 percent by volume molecular oxygen;

contacting the tetrahydrocannabinol molecule with a heat sink to condense the tetrahydrocannabinol molecule into a condensed tetrahydrocannabinol molecule in a liquid distillate that comprises the condensed tetrahydrocannabinol molecule and cannabinol at a molar ratio of greater than 100:1;

collecting the liquid distillate; and producing a product comprising tetrahydrocannabinol at a concentration of at least 55 percent by weight from the liquid distillate.

25. A method to chemically modify a cannabinoid molecule, comprising:

providing a composition comprising cannabinoids, wherein the composition comprises an extracted oil that was extracted from a plant material of the genus *Cannabis*, the extracted oil comprises the cannabinoids, the cannabinoids comprise a tetrahydrocannabinolic acid molecule, and the tetrahydrocannabinolic acid molecule comprises a carboxyl group;

coating a heated surface with the composition at a surface-area-to-volume ratio of the composition that is greater than 500 per meter, wherein the heated surface is a surface of a thin-film evaporator;

contacting the composition with sufficient energy from the heated surface to convert the tetrahydrocannabinolic acid molecule into (i) a carbon dioxide molecule and (ii) a tetrahydrocannabinol molecule in a gas phase;

contacting the tetrahydrocannabinol molecule with a heat sink to condense the tetrahydrocannabinol molecule into a condensed tetrahydrocannabinol molecule in a liquid distillate that comprises the condensed tetrahydrocannabinol molecule and cannabinol at a molar ratio of greater than 100:1;

collecting the liquid distillate; and producing a product comprising tetrahydrocannabinol at a concentration of at least 55 percent by weight from the liquid distillate.

26. A method to chemically modify a cannabinoid molecule, comprising:

providing a composition comprising cannabinoids, wherein the composition comprises an extracted oil that was extracted from a plant material of the genus *Cannabis*, the extracted oil comprises the cannabinoids, the cannabinoids comprise a tetrahydrocannabinolic acid molecule, and the tetrahydrocannabinolic acid molecule comprises a carboxyl group;

coating a heated surface with the composition at a surface-area-to-volume ratio of the composition that is greater than 500 per meter, wherein the heated surface is a surface of a thin-film evaporator;

contacting the composition with sufficient energy from the heated surface to convert the tetrahydrocannabinolic acid molecule into (i) a carbon dioxide molecule and (ii) a tetrahydrocannabinol molecule in a gas phase, wherein the sufficient energy is less than 0.004 kilowatt hours of energy per gram of the composition;

contacting the tetrahydrocannabinol molecule with a heat sink to condense the tetrahydrocannabinol molecule into a condensed tetrahydrocannabinol molecule in a liquid distillate that comprises the condensed tetrahydrocannabinol molecule and cannabinol at a molar ratio of greater than 100:1;

collecting the liquid distillate; and producing a product comprising tetrahydrocannabinol at a concentration of at least 55 percent by weight from the liquid distillate.

* * * * *